United States Patent [19]

Combs

[11] Patent Number: 5,753,655
[45] Date of Patent: May 19, 1998

[54] 1-ARYLSULPHONYL, ARYLCARBONYL AND ARYLTHIOCARBONYL PYRIDAZINO DERIVATIVES AND METHODS OF PREPARATION

[75] Inventor: Donald W. Combs, Piscataway, N.J.

[73] Assignee: Ortho Pharmaceutical Corporation, Raritan, N.J.

[21] Appl. No.: 728,882

[22] Filed: Oct. 10, 1996

[51] Int. Cl.$^6$ .......... A61K 31/50; C07D 237/26; C07D 491/04; C07D 495/04
[52] U.S. Cl. .......... 514/248; 544/234
[58] Field of Search .......... 544/234; 514/248

[56] References Cited

PUBLICATIONS

Advanced Organic Chemistry by Jerry March, pp. 382–384, 451–452 (1977).
Hogale et al, *Chemical Abstracts*, vol. 118, No. 213007 (1993).
Deshmurh et al, *Chemical Abstracts*, vol. 120, No. 323440 (1994).
McGuire et al, *Biochemistry*, vol. 13, pp. 319–322 (1974).
Holava et al, *J. Med. Chem.* 14, pp. 262–264 (1971).
Aubagnac et al, *Bull. Chem. Soc. France* pp. 2859–2868 (1972).

*Primary Examiner*—Emily Bernhardt
*Attorney, Agent, or Firm*—Ralph R. Palo

[57] ABSTRACT

1-Arylsulphonyl, arylcarbonyl and arylthiocarbonyl pyridazino derivatives and processes for making said derivatives are described. The novel derivatives are non-steroidal heterocyclic compounds which act as selective progestins and/or antiprogestins having a high in-vitro affinity for either the uterine, breast or bone progestin receptor. As such, the non-steroidal heterocyclic derivatives are useful in contraception, menopause, osteoporosis or endometriosis.

16 Claims, No Drawings

1-ARYLSULPHONYL, ARYLCARBONYL AND ARYLTHIOCARBONYL PYRIDAZINO DERIVATIVES AND METHODS OF PREPARATION

BACKGROUND OF THE INVENTION

Some intermediates in the synthesis of the claimed compounds are known. For example, 3,4-diazo-1,2,3,9,10,10a-hexahydrophenanthrene-2-one (A) and 3,4,4a,5,6,7-hexahydro-2H-benzo[6,7]cyclohepta[1,2c]pyridazine-2-one (B) are reported by Holava and Partyka. 2,4,4a,5-Tetrahydro-3H-indeno[1,2-c]pyridazine-3-one (C) are reported by Toma and Cignarella et al.

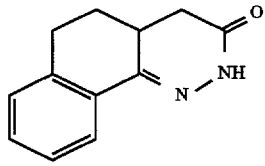

A

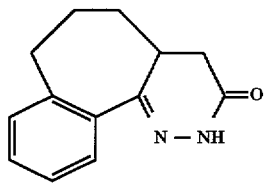

B

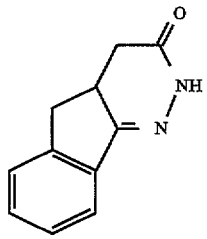

C

The synthesis of 7-bromo-4-methyl-1-tetralone (E), a compound related to intermediates used in this invention, from 4-methyl-1-tetralone (D) has been reported (verbally) by Prof. R. Danheiser at MIT. Although Danheiser describes the synthesis of a compound reported in the literature, his method is similar to the method used herein to prepare previously unknown compounds used to synthesize the compounds of this invention.

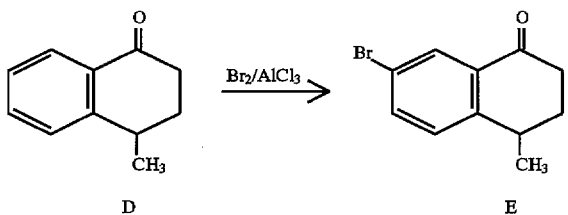

D        E

No trihalogenated benzocycloalkanones have been reported in the literature.

Of the dihalobenzocycloalkanones, only the 6,7-difluoro- and 6,7-dichlorotetralones are known but these are made by a different route. Owton, W. M. and Brunavs, M. *Synthetic Communications*. 21, 981, (1991).

No dibromobenzocycloalkanones are known.

All of the monobromotetralones are known except 8-bromo-1-tetralone.

None of the claimed compounds of the present invention have been disclosed.

DISCLOSURE OF THE INVENTION

The present invention is directed to compounds represented by formula I:

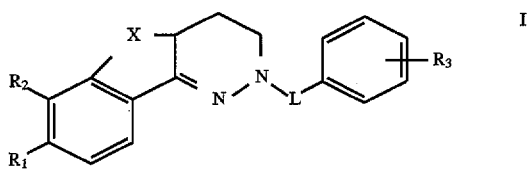

I wherein:

L is CO, CS or $SO_2$;

$R_1$ and $R_2$ are independently selected from any of H, halogen, alkyl ($C_1$–$C_6$), haloalkyl ($C_1$–$C_6$), nitro, cyano, carboxyl, and carboalkoxyl ($C_1$–$C_6$); provided that when L is $SO_2$, $R_1$ and $R_2$ are not simultaneously hydrogen;

$R_3$ is independently one, two or three of the following in any substitution pattern: H, halogen, alkyl ($C_1$–$C_6$), haloalkyl ($C_1$–$C_6$), nitro, carboxyl or carboalkoxyl ($C_1$–$C_6$);

X is a diradical of the formula $(CH_2)_n$ or Y—$(CH_2)$n–1 where n is an integer from 1 to 3; and Y is O or S.

For the purpose of this invention unless otherwise stated herein, and when used alone or with another alkyl is defined as 1–6 carbon atoms which may be branched in which case there are at least 3 carbon atoms or unbranched. Halogen is defined as chlorine, bromine, fluorine or iodine. Alkoxy refers to groups derived from alcohols having 1–6 carbon atoms and haloalkyl is defined as containing an alkyl group having 1–3 carbon atoms, such as trifluoromethyl.

The compounds of this invention are nonsteroidal heterocycles which can act as selective progestins and/or antiprogestins having a high in-vitro affinity for either the uterine, breast or bone progestin receptor as well as biological activity by intravenous, subcutaneous and oral routes. As a result, they may be useful as therapeutics in connection with contraception, menopause, endometriosis, breast cancer, cyclesynchrony, pregnancy termination, labor induction or osteoporosis.

DETAILED DESCRIPTION OF THE PREFERRED EMBODIMENT(S)

More specifically, the present invention relates to a series of nonsteroidal heterocyclic derivatives, the activity of which mimics that of progestins and/or antiprogestins having a high in vitro affinity for either the uterine or breast or bone progestin receptor.

The preferred compounds of this invention are those wherein L is $SO_2$, at least one of $R_1$ and $R_2$ is halogen, $R_3$ is halogen and/or $CF_3$, and X is $(CH_2)$n, where n=1–3. Another preferred group of the compounds of this invention include those compounds wherein L is CO or CS, $R_1$ and $R_2$ are hydrogen, $R_3$ is 3,4-dichloro, and X is $(CH_2)_n$, where n=1–3.

The compounds of the present invention may be prepared by the following reaction Scheme 1:

REACTION SCHEME 1

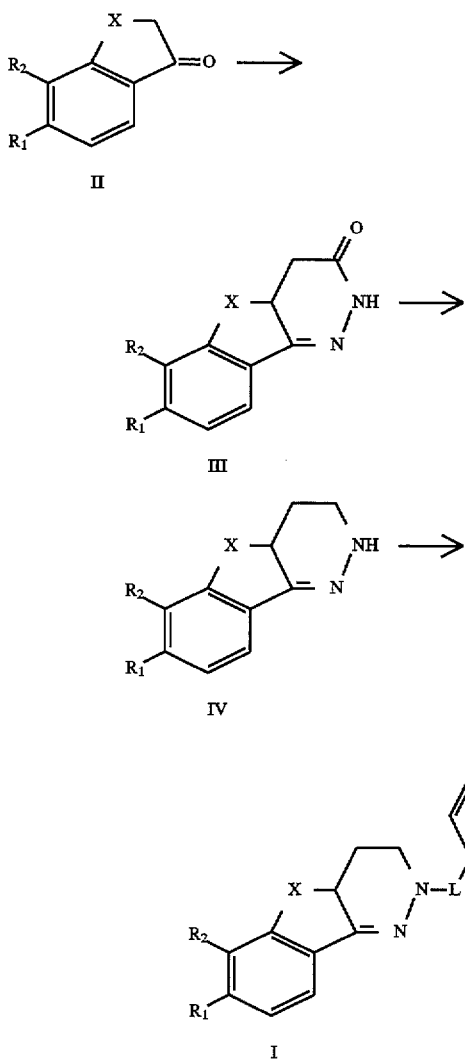

As can be seen from Reaction Scheme I, an appropriately substituted benzocycloalkanone (II) is converted to the cyclic acylhydrazone (III) by a means known in the art such as the method of Holava and Partyka (*J. Med. Chem.* 14, 262, (1971)). Generally, this comprises conversion of II to an αβ, unsaturated keto acid using glyoxylic acid and base, followed by the reduction of the unsaturation by heating with zinc in acetic acid and treatment of the reduced ketoacid with hydrazine to form III.

The substituted cyclic acylhydrazone (III) is then converted to the cyclic hydrazone (IV) by reaction with a reducing agent such as, for example, lithium aluminum hydride or diborane in a suitable solvent such as tetrahydrofuran (THF) by conventional means such as described by J-L. Aubagnac, J. Elguero, R. Jacquier and R. Robert in *Bull. Chem. Soc. France* 2859, (1972).

The resultant cyclic hydrazone (IV) is acylated with an appropriately substituted benzoyl halide or sulfonyl halide in a suitable solvent such as pyridine or in an organic solvent such as THF or toluene with a base such as triethylamine to form the nonsteroidal heterocyclic derivative (I).

The product is isolated and purified by techniques known to those skilled in the art such as, for example, by pouring the reaction mixture into a dilute acid such as, for example, hydrochloric acid, and extracting the mixture with an organic solvent such as methylene chloride or ethyl acetate. The organic layer is concentrated and the residue is crystallized or purified by chromatography over silica gel. The fractions containing the product are evaporated and the residue recrystallized to afford the desired compounds.

The amides obtained by this method can be converted to the thioamides (L=CS) by reaction with Lawesons Reagent or $P_2S_5$ in toluene.

Some of the halogenated starting materials are not known in the literature. These compounds can be prepared by the route shown in Reaction Scheme 2.

REACTION SCHEME 2

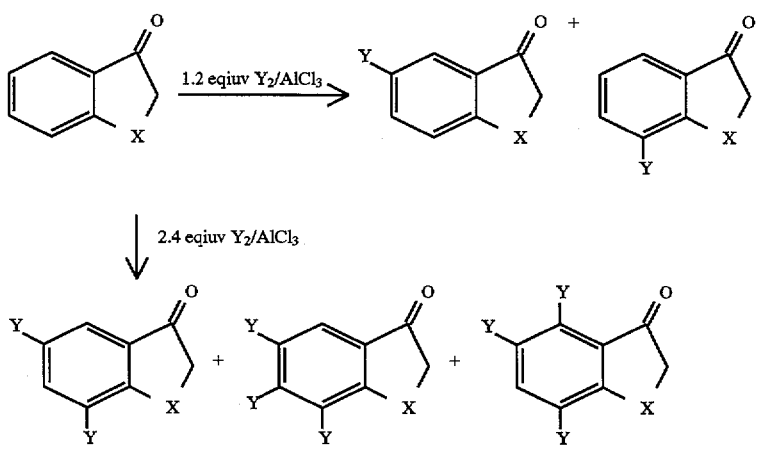

As shown, addition of 1.2 equivalents of halogenating agent in the presence of aluminum chloride affords two isomeric monohalobenzocycloalkanones where the halogen is introduced meta to the keto group. The addition of greater than 2 equivalents of halogenating agent in the presence of aluminum chloride affords the dihalobenzocycloalkanones as well as two isomeric trihalobenzocycloalkanones. Additionally, monohalobenzocycloalkanones can be halogenated with a different halogen to afford mixed substitutions such as for example: 6-bromo-5-chloro-1-tetralone or 5-chloro-7-iodo-1-tetralone.

The activity of the compounds of the present invention is demonstrated by screening in a progestin receptor binding assay and an Ex Vivo Progestational assay.

Progestin Receptor Binding

The procedure used is essentially that of J. L. McGuire, C. D. Bariso and A. P. Shroff in Biochemistry 13, 319 (1974).

Uteri from New Zealand rabbits (1.5 to 2.5 kg) are placed in a cold buffer A (0.01M Tris-HCl, pH 8.0, 0.001M EDTA, 0.25M sucrose). The uteri are minced, washed and homogenized in cold buffer A. The homogenate (2 g wet tissue/mL buffer) is centrifuged at 200,000 G for 1 h at 4° C. The high speed supernatant fraction is used as the receptor preparation.

A competitive binding assay is performed by mixing $^3$H-R5020 with the receptor preparation and adding a known amount of unlabelled compound. This mixture is incubated at 4° C. for 18 h. The compounds bound to the receptor are separated from those free in solution using dextran coated charcoal and the amount of isotope bound to the receptor is determined. A depression of 20% or greater from control isotope binding is considered significant.

A similar method may be used to determine binding affinities to progestin receptor derived from breast or bone tissue.

Ex Vivo Progestational Test

The incorporation of $^3$H-thymidine into T47-D cells was used to test the effect of compounds on T47-D cell proliferation. Compounds of the present invention have utility to treat in vivo progestin modulated biological conditions where they demonstrate a sufficient effect on the growth of T47-D cells.

A similar method was used to measure the effect of test compounds on TE85 human bone cells.

T47-D (human breast line) was used employing standard sterile techniques. Cells were maintained in RPMI 1640 medium supplemented with fetal bovine serum (10%) and insulin (0.2 I.U./ml). Cells were trypsinized and passaged using standard procedures.

Cells were plated in 96-well microtiter plates by incubation in RPMI medium (phenol red-free, insulin-free, 5% charcoal treated fetal bovine serum) at 37° C. in an atmosphere of 95% air/5% $CO_2$. Approximately 48 hours later, spent medium was replaced by fresh medium containing test compounds dissolved in DMSO (0.1% final concentration) and the cells were incubated for approximately 22 hours. $^3$H-Thymidine was added and the incubation allowed to proceed for another 4 hours. The test was then stopped with the addition of excess unlabeled thymidine. Cells were washed free of soluble thymidine, trypsinized and harvested by standard procedures. The amount of $^3$H-thymidine incorporated into DNA was determined by liquid scintillation counting. The primary standards were promegestone, a potent synthetic progestin and RU486, an antiprogestin. Test compounds were generally screened at concentrations ranging from 0.1 to 1000 nM. A compound was considered active if it stimulated or inhibited thymidine incorporation. Results were expressed as the concentration of test compounds needed to increase proliferation 2 times over control ($SC^{200}$) or the concentration needed to inhibit promegestone induced proliferation by 50% ($EC_{50}$). A value less than 1000 nM was considered active.

Aspects of the application of the procedure used are described in the following: C. Christensen, D. Gunter, D. Saunders and V. Malviya, *Gynecol. Oncol.*, 28, 25 (1987); J. Puzas, R. Drivdahl, G. Howard and D. Baylink, *Proc. Soc. Exp. Biol. Med.*, 166, 113 (1981); and I. Keydar, L. Chen, S. Karby, F. Weiss, J. Delarea, M. Raduy, S. Chaitcik and H. Brenner, *Eur. J. Cancer*, 15, 659 (1979).

TABLES

Table 1 shows examples of the invention with molecular formulas, melting points, the binding affinity expressed as the concentration of compound in nanomoles per liter ($\times 10^{-9}$M) required to displace 50% of $H^3$ labeled R5020 from the rabbit uterine cytosolic progestin receptor (PR)($IC_{50}$), and the ability to proliferate or to inhibit the R5020 induced proliferation of T47D human breast carcinoma cells (T47D). If there is no value reported in the T47D column that particular compound was not tested.

Tables 2 and 3 show several examples of the invention with molecular formulas, melting points, and activity expressed as the average increase in bone cell proliferation at 5 concentrations (CP) or as the concentration of compound in nanomoles per liter ($\times 10^{-9}$M) required to displace 50% of $I^{125}$ labeled vinyl nortestosterone (VNT) from the human bone progestin receptor (BPR) ($IC_{50}$). If there is no value reported in the CP column that particular compound was not tested.

TABLE 1

SULFONAMIDES

| # | R1 | R2 | X | R3 | PR | T47D | Formula | MP |
|---|----|----|----|----|-----|------|---------|-----|
| 1 | H | Br | (CH$_2$)$_3$ | 4-I | 76 | | C$_{19}$H$_{18}$BrIN$_2$O$_2$S | 180–1 |
| 2 | H | Br | (CH$_2$)$_2$ | 4-I | 10 | | C$_{18}$H$_{16}$BrIN$_2$O$_2$S | 197–8 |
| 3 | Br | Br | (CH$_2$)$_2$ | 4-I | 2.4 | +337 | C$_{18}$H$_{15}$BrIN$_2$O$_2$S | 202–3 |
| 4 | Cl | H | (CH$_2$)$_2$ | 4-I | 8.3 | −654 | C$_{18}$H$_{10}$ClIN$_2$O$_2$S | 194–6 |
| 5 | Br | H | (CH$_2$)$_2$ | 2,5-diCl | 34 | −495 | C$_{18}$H$_{15}$Cl$_3$N$_2$O$_2$S | 186–7 |

+ indicates agonist $SC_{200}$ nM (the concentration stimulating 2-fold above control)
− indicates antagonist $EC_{50}$ nM against R5020 induced proliferation

TABLE 2

AMIDES

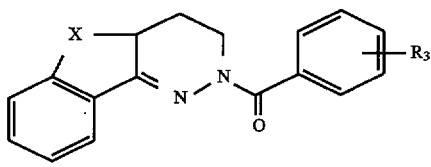

| # | X | R3 | CP | BPR | Formula | MP |
|---|---|---|---|---|---|---|
| 6 | $(CH_2)_2$ | 3,4-diCl | 115 | | $C_{19}H_{16}Cl_2N_2O$ | 154–5 |
| 7 | $(CH_2)_3$ | 3,5-diCl | 120 | 8.4 | $C_{20}H_{18}Cl_2N_2O$ | 115–6 |
| 8 | $(CH_2)_3$ | 3,4-diF | | 4.8 | $C_{20}H_{18}F_2N_2O$ | 117–8 |
| 9 | $(CH_2)_3$ | 3,4-diCl | 123 | 107 | $C_{20}H_{18}Cl_2N_2O$ | 136–7 |
| 10 | $(CH_2)_2$ | 3,4-diF | 112 | | $C_{19}H_{16}F_2N_2O$ | 146–7 |
| 11 | $(CH_2)_2$ | 3,5-diCl | 113 | 11.6 | $C_{19}H_{16}Cl_2N_2O$ | 141–2 |
| 12 | $OCH_2$ | 3,4-diCl | 107 | 3.6 | $C_{18}H_{14}Cl_2N_2O_2$ | 166–7 |
| 13 | $SCH_2$ | 3,4-diCl | | 50 | $C_{18}H_{14}Cl_2N_2OS$ | 145–6 |
| 14 | $CH_2$ | 3,4-diCl | | 9.0 | $C_{18}H_{14}Cl_2N_2O$ | 122–4 |

TABLE 3

THIOAMIDES

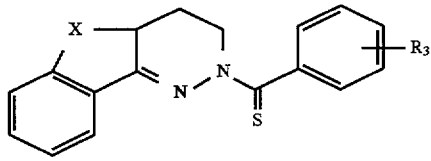

| # | X | R3 | CP | BPR | Formula | MP |
|---|---|---|---|---|---|---|
| 15 | $(CH_2)_3$ | 3,5-diCl | 109 | 23.3 | $C_{20}H_{18}Cl_2N_2S$ | 149–50 |
| 16 | $(CH_2)_3$ | 3,4-diF | 111 | | $C_{20}H_{18}F_2N_2S$ | 134–6 |
| 17 | $(CH_2)_3$ | 3,4-diCl | 115 | 32 | $C_{20}H_{18}Cl_2N_2S$ | 140–1 |
| 18 | $(CH_2)_2$ | 3,4-diF | | | $C_{19}H_{16}F_2N_2S$ | 170–1 |
| 19 | $(CH_2)_2$ | 3,4-diCl | 87 | 44.3 | $C_{19}H_{16}Cl_2N_2S$ | 110–1 |
| 20 | $(CH_2)_2$ | 3,5-diCl | 103 | 10.2 | $C_{19}H_{16}Cl_2N_2S$ | 162–3 |
| 21 | $OCH_2$ | 3,4-diCl | | 2.0 | $C_{18}H_{14}Cl_2N_2OS$ | 187–8 |
| 22 | $CH_2$ | 3,4-diCl | | 0.5 | $C_{18}H_{14}Cl_2N_2S$ | 138–40 |

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g. intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions), or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients may be employed, for example, to aid solubility or for preservative purposes; injectable suspensions may also be prepared, in which case appropriate liquid carriers, suspending agents and the like may be employed. The pharmaceutical compositions of the present invention for use in the treatment of any of contraception, menopause, endometriosis, breast cancer, cyclesynchrony, pregnancy termination, labor induction or osteoporosis are possible indications. the most likely are endometriosis, contraception and osteoporosis will generally contain a dosage unit, e.g. tablet, capsule, powder and the like, from about 1 to about 500 mg/kg/day and preferably from about 10 to about 100 mg/kg/day of the active ingredient. The exact dose may vary depending upon the age and condition of the patient and the particular condition being tested.

EXAMPLES

I. Preparation of Starting Materials and Intermediates Used in Preparing Final Products of the Invention The following Sections A, B and C contain a description of the preparation of certain starting materials and intermediates useful in the preparation of the compounds of the present invention.

A. Preparation of Halobenzocyclanones

In the following examples, N-bromosuccinimide can be substituted for bromine and N-chlorosuccinimide or chlorine can be used to make the chloro compounds. N-iodosuccinimide affords the iodo analogs.

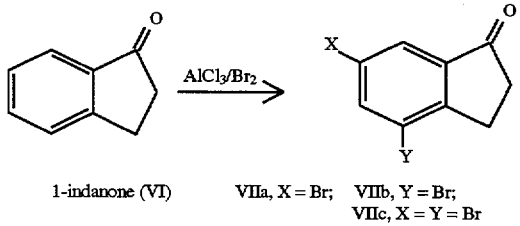

1-indanone (VI)   VIIa, X = Br;   VIIb, Y = Br;
                                   VIIc, X = Y = Br 6-Bromoindan-1-one (VIIb) and 4-bromoindan-1-one (VIIa).

A 250 mL three-necked round bottom flask was equipped with a water cooled Liebig condenser, a mechanical stirrer and a pressure-equalized addition funnel protected by means of drying tubes. The flask was charged with anhydrous aluminum chloride (16.6 g, 0.125 moles) and stirred while 1-Indanone (VI) (6.60 g, 0.05 moles), which had been ground to a fine powder with a mortar and pestle was added in two portions over 3 minutes. Copious evolution of HCl gas was accompanied by a moderate exotherm and the mixture rapidly became a dark brown, homogenous slurry which was stirred for an additional 10 minutes.

Bromine (3.1 ml, 0.06 moles) was added dropwise to the well stirred mixture over a 10 minute period. After all the bromine had been added, the molten mixture was heated in a water bath to 80° C. for 5 minutes. While still hot, the mixture was poured into 100 g of crushed ice and 20 ml of concentrated hydrochloric acid. The ice mixture was then stirred for 10 minutes, diluted with 100 ml of water and extracted with ether (2×200 mL). The combined ether extracts were washed with water (2×100 mL) and dried over anhydrous sodium sulfate and concentrated to give 10.6 g of a red oil which crystallized on standing at room temperature.

Product analysis by GC-MS showed a 1:1 mixture of monobromo isomers. The material was chromatographed on a silica gel column (45×10 cm ) using n-hexane/THF (8:1) thereby separating the isomers. The separated isomers were each recrystallized from hexane to give 3.8 g of 6-bromoindan-1-one (VIIa) and 4.0 g of 4-bromoindan-1-one (VIIb).

VIIa: yield 37.7%; mp 108°–109° C.,light yellow prisms; IR (KBr) 1712 cm⁻¹; 1H NMR (CDCl₃) δ2.70–2.74 (m, 2H), 3.08–3.12 (m, 2H),7.35–7.38 (d,1H), 7.66–7.70 (dd, 1H), 7.87–7.88 (d, 1H) ; ms m/z 211; Anal.Calcd. for $C_9H_7BrO$: C, 51.22; H,3.34. Found: C, 51.10; H, 3.25.

VIIb: yield 35.8%; mp90°–92° C.,light yellow prisms; IR (KBr) 1709 cm⁻¹; 1H NMR (CDCl₃) δ2.71–2.75 (m, 2H), 3.06–3.09 (m, 2H), 7.25–7.30 (dd, 1H), 7.69–7.71 (d, 1H), 7.74–7–76 (dd, 1H); ms m/z 211; Anal.Calcd. for $C_9H_7BrO$: C, 51.22; H,3.34. Found: C, 50.38; H, 3.24.

7-Bromo-1-tetralone (IXa) and 5-bromo-1-tetralone (IXb)

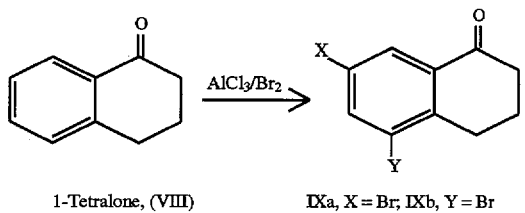

1-Tetralone, (VIII)     IXa, X = Br; IXb, Y = Br

1-Tetralone (VII) (7.3 g, 0.05 mol) was added dropwise to anhydrous aluminum chloride (16.6 g, 0.125 mol) with vigorous stirring over 3 minutes. Bromine (3.71 mL, 0.06 mol) was added to the resulting slurry over 10 minutes. The mixture was heated to 80° C. for 5 minutes after the addition of bromine was complete and the still molten mixture was poured into 150 g of crushed ice containing 20 ml of 12N HCl. Following the same work up as for example 1, 10.85 g of a brown oil was obtained. The oil was chromatographed on a silica gel column (45×10 cm ) using hexane:THF (8:1). The separated isomers were each recrystallized from hexane to give 4.2 g of 7-bromo-1-tetralone (IXa) and 4.5 g of 5-bromo-1-tetralone (IXb).

IXa: yield 37.2%; mp74°–75° C.,light yellow prisms; IR (KBr) 1676 cm⁻¹; 1H NMR (CDCl₃) δ2.09–2.18 (m, 2H), 2.63–2.67 (t, 2H), 2.89–2.93 (t, 2H), 7.13–7.16 (d, 1H), 7.55–7.58 (dd, 1H), 8.14–8.15 (d, 1H); ms m/z 225; Anal.Calcd. for $C_{10}H_9BrO$: C, 53.36; H, 4.03. Found: C, 53.14; H, 3.96.

IXb: yield 39.8%; mp 45°–46° C.,light yellow prisms; IR (KBr) 1679 cm⁻¹; 1H NMR (CDCl₃) δ2.11–2.20 (m, 2H), 2.62–2.67 (t, 2H), 2.94–3.03 (t, 2H), 7.15–7.21 (dd, 1H), 7.71–7.74 (dd, 2H), 7.99–8.02 (dd, 1H); ms m/z225; Anal.Calcd. for $C_{10}H_9BrO$: C, 53.36; H, 4.03. Found: C, 52.97; H, 3.94.

5,7-dibromo-1-tetralone (IXc), 5,6,7-tribromo-1-tetralone (IXd) and 5,7,8-tribromo-1-tetralone (IXe)

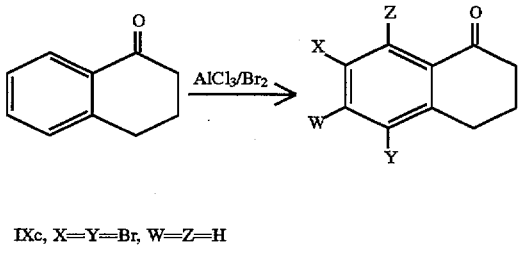

IXc, X=Y=Br, W=Z=H

IXd, X=Y=W=Br, Z=OH; IXe, X=Y=Z=Br, W=H

Bromine (7.42 g, 0.12 moles) was added dropwise to a slurry generated from anhydrous aluminum chloride (16.6 g, 0.125 mol) and 1-tetralone (VII) (0.05 mol) as in example 1. This yielded 15.0 g of a brown oil on work up which crystallized on standing. GC-MS showed a mixture of 87% dibrominated product and 13% of a 1:1 mixture of tribrominated isomers. Chromatography and recrystallization from hexane gave 7.7 g.

IXc: yield 51%; mp 60°–61° C., light yellow prisms; IR (KBr) 1690 cm⁻¹; 1H NMR (CDCl₃) δ2.11–2.20 (m, 2H), 2.62–2.66 (dd, 2H), 2.93–2.97 (t, 2H, J=6.2 Hz), 7.88 (d, 1H, J=2 Hz), 8.13 (d, 1H, J=2Hz); ms m/z 304; Anal.Calcd. for $C_{10}H_8Br_2O$: C, 39.51; H,2.65. Found: C, 39.41; H, 2.49.

8-Bromo-1-benzosuberone (XIa) and 6-bromo-1-benzosuberone (XIb)

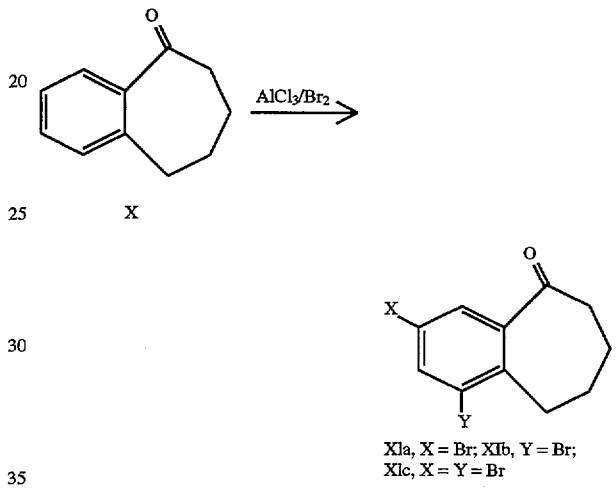

XIa, X = Br; XIb, Y = Br;
XIc, X = Y = Br

Following the general procedures detailed above for the preparation of the bromotetralones, a mixture of benzosuberone (X) (8.01 g, 0.05 mol), aluminum chloride (16.6 g, 0.125 mol), and bromine (3.07 mL, 0.06 mol) yielded 11.87 g of a brown oil after the usual work up. GC-MS showed a 1:1 mixture of monobromo isomers containing 2% of the dibromo isomer.

XIa: yield 30%; mp 38°–38.5° C., off white powder; ms m/z 239; Anal.Calcd. for $C_{11}H_{11}BrO$: C, 55.25; H,4.64. Found: C, 54.83; H, 4.62.

XIb: yield 32%; clear oil bp 101–105 @ 0.12 mmHg; ms m/z =239; Anal.Calcd. for $C_{11}H_{11}BrO$: C,55.25; H,4.64. Found: C,55.32; H, 4.59.

5,6-dibromo-1-tetralone XIIa and 6,7-dibromo-1-tetralone XIIb

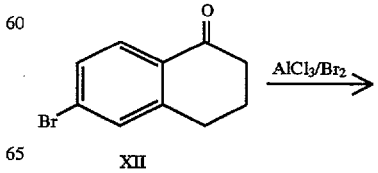

XII

-continued

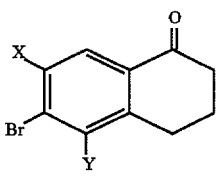

XIIa, Y = Br, X = H
XIIb, X = Br, Y = H

Following the same methods detailed above for the bromination of tetralone, a mixture of 6-bromo-1-tetralone XII (2 g, mmol) aluminum chloride (16.6 g, 0.125 mol), and bromine (3.07 mL, 0.06 mol) yielded 1.87 g of a brown oil after the usual work up.

B. Preparation of Cyclic Acylhydrazones 3,4-Diazo-1,2,3,9,9a-tetrahydrofluorene-2-one (XIII)

The title compound was prepared as described in Toma, L., Cignarella, G., Barlocco, D. and Ronchetti, F. *J. Med. Chem.*, 33,1591–4, 1990.

3,4-Diazo-1,2,3,9,10,10a-hexahydrophenanthrene-2-one (XIV)

The title compound was prepared as described in Holava, H. M. and Partyka, R. A. *J. Med. Chem.* 14, 262, (1971).

3,4,4a,5,6,7-Hexahydro-2H-benzo[6,7]cyclohepta[1.2c]pyridazine-2-one (XV)

The title compound was prepared as described in Holava, H. M. and Partyka, R. A. *J. Med. Chem.* 14, 262, (1971).

8-Bromo-3,4-diazo-1,2,3,9,10,10a-hexahydrophenanthrene2-one (XVI)

The title compound was prepared by treating 5-Bromo-1-tetralone (IXb) (20 mmol) with glyoxylic acid (20 mmol), the product reduced with excess zinc in acetic acid and treated with excess hydrazine by conventional means as in Holava, H. M. and Partyka, R. A. *J. Med. Chem.* 14, 262, (1971) to give the title compound.

7,8-Dibromo-3,4-diazo-1,2,3,9,10,10a-hexahydrophenanthrene2-one (XVII)

The title compound was prepared by treating 5,6-Dibromo-1-tetralone (XIIa) (10 mmol) with glyoxylic acid (10 mmol), the product reduced with excess zinc in acetic acid and thereafter treated with excess hydrazine as in Holava, H. M. and Partyka, R. A. *J. Med. Chem.* 14, 262, (1971) to give the title compound.

7-Chloro-3,4-diazo-1,2,3,9,10,10a-hexahydrophenanthrene-2-one (XVIII)

The title compound was prepared by treating 6-Chloro-1-tetralone (Rosowsky, A., Chaykovsky, M., Yeager, S. A., et al *J. Het. Chem.* 8, 809, (1971)) 50 mmol with glyoxylic acid 50 mmol and base then reducing with excess zinc in acetic acid and thereafter treating with excess hydrazine as in Holava, H. M. and Partyka, R. A. *J. Med. Chem.* 14, 262, (1971) to give the titled compound.

8-Bromo-3,4,4a,5,6,7-hexahydro-2H-benzo[6,7]cyclohepta[1,2c] pyridazine-2-one (XIX)

The title compound was prepared by treating 6-Bromo-1-benzosuberone XIb with glyoxylic acid, then reducing with excess zinc in acetic acid and thereafter treating with excess hydrazine as in Holava, H. M. and Partyka, R. A. *J. Med. Chem.* 14, 262, (1971) to give the titled compound.

C. Preparation of Cyclic Hydrazones 3,4-Diazo-1,2,3,9,10,10a-hexahydrophenanthrene (XX)

3,4-Diazo-1,2,3,9,10,10a-hexahydrophenanthrene2-one (XIV) (2.5 g, 12.5 mmol) was dissolved in THF and 1 equivalent of lithium aluminum hydride (21 mL, 1M solution in THF) added dropwise. After 30 min at 22° C., 15% NaOH solution was added dropwise and the gelatinous precipitate filtered. The filtrate was dried over magnesium sulfate and filtered and evaporated to dryness to give an oil which was used as the starting material without further purification.

7-Chloro-3,4-diazo-1,2,3,9,10,10a-hexahydrophenanthrene (XXI)

7-Chloro-3,4-diazo-1,2,3,9,10,10a-hexahydrophenanthrene2-one (XVIII) was dissolved in THF and 1 equivalent of lithium aluminum hydride (1M solution in THF) added dropwise. After 30 min at 22° C. 15% NaOH solution was added dropwise and the precipitate filtered. The filtrate was dried over magnesium sulfate, filtered and evaporated to dryness to give an oil which was used as the starting material without further purification.

8-Bromo-3,4,4a,5,6,7-hexahydro-2H-benzo[6,7]cyclohepta[1,2c] pyridazine (XXII)

8-Bromo-3,4,4a,5,6,7-hexahydro-2H-benzo[6,7]cyclohepta[1,2c] pyridazine-2-one (XIX) (1 g, 3.4 mmol) was dissolved in THF and 2 equivalents of diborane (1M solution in THF) added dropwise. After 2 h at 22° C. the reaction was quenched with 1 mL of 6M HCl and neutralized with 50% NaOH solution then dried over magnesium sulfate and filtered. The filtrate was evaporated to dryness to give an oil which was used as is without further purification.

8-Bromo-3,4-diazo-1,2,3,9,10,10a-hexahydrophenanthrene (XXIII)

8-Bromo-3,4-diazo-1,2,3,9,10,10a-hexahydrophenanthrene2-one (XVI) (1.0 g, 3.6 mmol) was dissolved in THF (100 mL) and 2 equivalents of diborane (1M solution in THF) added dropwise. After 1 h at 22° C. the reaction was heated on a steam bath for 5 min then quenched with 1 mL of 6M HCl and neutralized with 15% NaOH solution then dried over magnesium sulfate and filtered. The filtrate was evaporated to dryness to give an oil which was used as is without further purification.

7,8-Dibromo-3,4-Diazo-1,2,3,9,10,10a-hexahydrophenanthrene (XXIV)

7,8-Dibromo-3,4-diazo-1,2,3,9,10,10a-hexahydrophenanthrene2-one (XVII) (0.71 g, 1.98 mmol) was suspended in THF and 2 equivalents of diborane (3.96 mL of 1M solution in THF) added dropwise at 22° C. The mixture was heated briefly to 45° C. to dissolve all solids then stirred at room temperature for 60 h. The reaction was quenched with 1 mL of 6M HCl and neutralized with 50% NaOH solution then dried over magnesium sulfate and filtered. The filtrate was evaporated to dryness to give an oil which was used as the starting material without further purification.

3,4-Diazo-1,2,3,9,9a-tetrahydrofluorene (XXV)

3,4-Diazo-1,2,3,9,9a-tetrahydrofluorene-2-one (XIII) (3.5 g, 17.5 mmol) was dissolved in THF and 1 equivalent of lithium aluminum hydride (1M solution in THF) added dropwise. After 30 min at 22° C. 15% NaOH solution was added dropwise and the gelatinous precipitate filtered. The filtrate was dried over magnesium sulfate and filtered and evaporated to dryness to give an oil which was used as the starting material without further purification.

3,4-Diazo-9-oxa-1,2,3,9,10,10a-hexahydrophenanthrene (XXVI)

3,4-Diazo-9-oxa-1,2,3,9,10,10a-hexahydrophenanthrene-2-one (15 mmol) prepared as described in (Cignarella, G.; Barlocco, D.; Curzu, M. M.; Pinna, G. A.; Cazzulani, P.; Cassin, M.; Lumachi, B. *Eur. J. Med. Chem.* 25(9), 749–56, (1990)), was reduced as above with 2 equiv. of diborane.

3,4-Diazo-9-thia-1,2,3,9,10,10a-hexahydrophenanthrene (XXVII)

3,4-Diazo-9-thia-1,2,3,9,10,10a-hexahydrophenanthrene-2-one (10 mmol) prepared as described in (Nakao, Tohru; Tanaka, Hiroshi; Morimoto, Yasuto; Takehara, Shuzo; Demizu, Kenichi; Tahara, Tetsuya *Yakugaku Zasshi*, 110 (12), 922–31, (1990)) was reduced as above with 2 equiv. of diborane.

The following examples are used to illustrate the present invention but are not intended to limit the scope of the invention.

EXAMPLES

Example 1

8-Bromo-3,4,4a,5,6,7-hexahydro-2-(4-iodobenzenesulfonyl)-2H-benzo[6,7]cyclohepta[1,2c]pyridazine 8-Bromo-3,4,4a,5,6,7-hexahydro-2H-benzo[6,7]cyclohepta [1,2c]pyridazine (XIX) (1.0 g, 3.6 mmol) and 4-iodobenzenesulfonyl chloride (1.1 g, 3.6 mmol) were combined in a solution of 50 mL of dichloromethane and 50 mL of pyridine. The mixture was stirred at 22° C. for 64 h turning a deep red color. The mixture was concentrated at reduced pressure and the pyridine solution poured into 6M HCl and ice and extracted with dichloromethane. The organic layer was concentrated at reduced pressure and filtered through silica gel eluted with dichloromethane to give 1.3 g of off-white solid which was recrystallized from isopropanol/chloroform to give a white solid with mp 180°–181° C.

Calc for: $C_{19}H_{18}BrIN_2O_2S$: C, 41.85, H, 3.33, N, 5.14. Found: C, 41.68, H, 3.27, N, 5.03.

Example 2

8-Bromo-3,4-diazo-1,2,3,9,10,10a-hexahydro-3-(4-iodobenzenesulfonyl)phenanthrene 8-Bromo-3,4-diazo-1,2,3,9,10,10a-hexahydrophenanthren (XXI) (1.0 g, 3.77 mmol) and 4-iodobenzenesulfonyl chloride (1.14 g, 3.77 mmol) were combined in 100 mL of pyridine. The mixture was stirred at 22° C. for 16 h turning a deep red color. The mixture was then poured into 6M HCl and ice and extracted with dichloromethane. The organic layer was concentrated at reduced pressure and filtered through silica gel eluted with dichloromethane to give 0.3 g crude material which was recrystallized from hexane to give 0.28 g of an off-white solid with mp 197°–198° C.

Calc for: $C_{18}H16BrIN_2O_2S$: C, 40.76, H, 3.04, N, 5.27. Found: C, 40.59, H, 2.89, N, 5.06.

Example 3

7,8-Dibromo-3,4-diazo-1,2,3,9,10,10a-hexahydro-3-(4-iodobenzenesulfonyl)phenanthrene 7,8-Dibromo-3,4-diazo-1,2,3,9,10,10a-hexahydrophenanthrene (XVII) (0.7 g, 1.9 mmol) and 4-iodobenzenesulfonyl chloride (0.65 g, 2.1 mmol) were combined in 100 mL of pyridine. The mixture was stirred at 22° C. for 16 h turning a deep red color. The mixture poured into 6M HCl and ice and extracted with dichloromethane. The organic layer was concentrated at reduced pressure and filtered through silica gel eluted with dichloromethane to give crude material which was recrystallized from hexane to give 0.1 g of a white solid with mp 202°–203° C.

Calc for: $C_{18}H_{15}Br_2IN_2O_2S$: C, 35.44, H, 2.48, N, 4.59. Found: C, 35.54, H, 2.47, N, 4.61.

Example 4

7-Chloro-3,4-diazo-1,2,3,9,10,10a-hexahydro-3-(4-iodobenzenesulfonyl)phenanthrene 7-Chloro-3,4-diazo-1,2,3,9,10,10a-hexahydrophenanthrene (XXI) (1.1 g, 5.0 mmol) and 4-iodobenzenesulfonyl chloride (1.2 g, 3.9 mmol) were combined in a solution of 50 mL of dichloromethane and 50 mL of pyridine. The mixture was stirred at 22° C. for 20 h turning a deep red color. The mixture was concentrated at reduced pressure and the pyridine solution was poured into 6M HCl and ice and extracted with dichloromethane. The organic layer was concentrated at reduced pressure and filtered through silica gel eluted with dichloromethane to give an off-white solid which was recrystallized from hexane to give 0.5 g of a white solid with mp 194°–196° C.

Calc for: $C_{18}H_{10}ClIN_2O_2S$: C, 44.42, H, 3.31, N, 5.76. Found: C, 44.73, H, 3.24, N, 5.31.

Example 5

7-Chloro-3,4-diazo-1,2,3,9,10,10a-hexahydro-3-(2,5-dichlorobenzenesulfonyl)phenanthrene 7-Chloro-3,4-diazo-1,2,3,9,10,10a-hexahydrophenanthrene (XXI) (1.0 g, 4.7 mmol) and 2,5-dichlorobenzenesulfonyl chloride (1.2 g, 4.9 mmol) were combined in 100 mL of pyridine. The mixture was stirred at 22° C. for 16 h turning a deep red color. The mixture was poured into 6M HCl and ice and extracted with dichloromethane. The organic layer was concentrated at reduced pressure and filtered through silica gel eluted with dichloromethane to give 0.5 g crude material which was recrystallized twice from hexane/chloroform to give 0.25 g of an off-white solid with mp 186°–187° C.

Calc for: $C_{18}H_{15}Cl_3N_2O_2S$: C,50.31, H, 3.52, N, 6.52. Found: C,50.23, H, 3.45, N, 6.44.

Example 6

3-(3,4-dichlorobenzoyl)-3,4-diazo-1,2,3,9,10,10a-hexahydrophenanthrene 3,4-diazo-1,2,3,9,10,10a-hexahydrophenanthrene (XXI) (2.67 g,14.3 mmol) and 3,4-dichlorobenzoylchloride (3.0 g) were combined in 100 mL of pyridine and stirred at 22° C. for 16 h. The mixture was poured into dichloromethane and washed twice with 2M HCl then dried over magnesium sulfate and filtered. The filtrate was concentrated and filtered through silica gel eluted with dichloromethane to give 3.7 g of an off-white solid mp 154°–5° C.

Calc for: $C_{19}H_{16}Cl_2N_2O$: C, 63.52, H, 4.49, N, 7.80. Found: C, 63.18, H, 4.39, N, 7.52.

Example 7

2-(3,5-dichlorobenzoyl)-3,4,4a,5,6,7-hexahydro-2H-benzo[6,7]cyclohepta[1,2c]pyridazine 3,4,4a,5,6,7-Hexahydro-2H-benzo[6,7]cyclohepta[1,2c]pyridazine (XV) (2.0 g, 10 mmol) and 3,5-dichlorobenzoylchloride (2.1 g, 10 mmol) were combined in 75 mL of dichloromethane and 5 mL of triethylamine added. The mixture was stirred at 22° C. for 16 h and evaporated to dryness at reduced pressure. The residue was dissolved in dichloromethane and washed with dilute HCl, dried over magnesium sulfate, filtered and chromatographed on silica gel eluted with dichloromethane to give 2.5 g of white solid with mp 115°–116° C.

Calc for: $C_{20}H_{18}Cl_2N_2O$: C, 64.35, H, 4.86, N, 7.50. Found: C, 64.38, H, 4.56, N, 7.56.

Example 8

2-(3,4-difluorothiobenzoyl)-3,4,4a,5,6,7-hexahydro-2H-benzo[6,7]cyclohepta[1,2c]pyridazine 3,4,4a,5,6,7-Hexahydro-2H-benzo[6,7]cyclohepta[1,2c]pyridazine (XV) (2.0 g, 10 mmol) and 3,4-difluorobenzoylchloride (2.1 g, 10 mmol) were combined in 75 mL of dichloromethane and 5 mL of triethylamine added. The mixture was stirred at 22° C. for 16 h and evaporated to dryness at reduced pressure. The residue was dissolved in dichloromethane and washed with dilute HCl, dried over magnesium sulfate, filtered and chromatographed on silica gel eluted with dichloromethane to give 2.8 g of pale yellow solid with mp 117°–118° C.

Calc for: $C_{20}H_{18}F_2N_2O$: C, 70.58, H, 5.33, N, 8.23. Found: C, 70.59, H, 5.26, N, 8.35.

Example 9

2-(3,4-dichlorobenzoyl)-3,4,4a,5,6,7-hexahydro-2H-benzo[6,7]cyclohepta[1,2c]pyridazine 3,4,4a,5,6,7-Hexahydro-2H-benzo[6,7]cyclohepta[1,2c]pyridazine (XV) (2.24 g, 11.2 mmol) and 3,4-dichlorobenzoylchloride (2.34 g, 11.2 mmol) were combined in 100 mL of dichloromethane and 10 mL of triethylamine added. The mixture was stirred at 22° C. for 16 h and evaporated to dryness at reduced pressure. The residue was dissolved in dichloromethane and washed with dilute HCl, dried over magnesium sulfate, filtered and chromatographed on silica gel eluted with dichloromethane to give 2.0 g of pale yellow solid with mp 136°–137° C.

Calc for: $C_{20}H_{18}Cl_2N_2O$: C, 64.35, H, 4.86, N, 7.50. Found: C, 64.29, H, 4.80, N, 7.39.

Example 10

3-(3,4-difluorobenzoyl)-3,4-diazo-1,2,3,9,10,10a-hexahydrophenanthrene 3,4-diazo-1,2,3,9,10,10a-hexahydrophenanthrene (XIV) (1.83 g, 9.82 mmol) and 3,4-difluorobenzoylchloride (1.73 g, 9.82 mmol) were combined in 75 mL of dichloromethane and 5 mL of triethylamine added. The mixture was stirred at 22° C. for 16 h and evaporated to dryness at reduced pressure. The residue was dissolved in dichloromethane and washed with dilute HCl, dried over magnesium sulfate, filtered and chromatographed on silica gel eluted with dichloromethane to give 1.4 g of white solid with mp 146°–147° C. Calc for: $C_{19}H_{16}F_2N_2O$: C, 69.93, H, 4.94, N, 8.58. Found: C, 69.78, H, 4.72, N, 8.79.

Example 11

3-(3,5-dichlorobenzoyl)-3,4-diazo-1,2,3,9,10,10a-hexahydrophenanthrene 3,4-diazo-1,2,3,9,10,10a-hexahydrophenanthrene (XIV) (2.67 g, 14.3 mmol) and 3,5-dichlorobenzoylchloride (3.0 g) were combined in 250 mL of dichloromethane and 10 mL of triethylamine added. The mixture was stirred at 22° C. for 1 h and evaporated to dryness at reduced pressure. The yellow residue was dissolved in dichloromethane and washed with dilute HCl, dried over magnesium sulfate, filtered and chromatographed on silica gel eluted with ether/dichloromethane (2:1) to give 3.0 g of white solid with mp 141°–142° C.

Calc for: $C_{19}H_{16}Cl_2N_2O$: C, 63.52, H, 4.49, N, 7.84. Found: C, 63.45, H, 4.14, N, 7.70.

Example 12

3-(3,4-dichlorobenzoyl)-3,4-diazo-9-oxa-1,2,3,9,10,10a-hexahydrophenanthrene 3,4-Diazo-9-oxa-1,2,3,9,10,10a-hexahydrophenanthrene XXVI (1.73 g, 9.2 mmol) and 3,4-dichlorobenzoylchloride (1.93 g) were combined in 200 mL of dichloromethane and 150 mL of triethylamine added. The mixture was stirred at 22° C. for 14 h and evaporated to dryness at reduced pressure. The yellow residue was dissolved in dichloromethane and washed with dilute HCl, dried over magnesium sulfate, filtered and chromatographed on silica gel eluted with dichloromethane to give 1.2 g of off-white solid with mp 166°–167° C.

Calc for: $C_{18}H_{14}Cl_2N_2O_2$: C, 59.85, H, 3.91, N, 7.75. Found: C, 59.83, H, 3.86, N, 7.73.

Example 13

3-(3,4-dichlorobenzoyl)-3,4-diazo-9-thia-1,2,3,9,10,10a-hexahydrophenanthrene 3,4-Diazo-9-thia-1,2,3,9,10,10a-hexahydrophenanthrene XXVII (1.33 g, 6.6 mmol) and 3,4-dichlorobenzoylchloride (1.38 g, 6.6 mmol) were combined in 100 mL of dichloromethane and 100 mL of triethylamine added. The mixture was stirred at 22° C. for 48 h and evaporated to dryness at reduced pressure. The yellow residue was dissolved in dichloromethane and washed with dilute HCl, dried over magnesium sulfate, filtered and chromatographed on silica gel eluted with ether/dichloromethane (2:1) to give 1.0 g of off-white solid which was recrystallized from benzene-hexane to give 0.84 g of a white solid with mp 145°–146° C.

Calc for: $C_{18}H_{14}Cl_2N_2OS$: C, 59.85, H, 3.91, N, 7.75. Found: C, 59.83, H, 3.86, N, 7.73.

Example 14

3-(3,4-dichlorobenzoyl)-3,4-diazo-1,2,3,9,9a-tetrahydrofluorene 3,4-diazo-1,2,3,9,9a-tetrahydrofluorene (XXV) (1.6 g, 9.3 mmol) and 3,4-dichlorobenzoylchloride (1.95 g, 9.3 mmol)

were combined in 100 mL of dichloromethane and 10 mL of triethylamine added. The mixture was stirred at 22° C. for 16 h and evaporated to dryness at reduced pressure. The residue was dissolved in dichloromethane and washed with dilute HCl, dried over magnesium sulfate, filtered and chromatographed on silica gel eluted with dichloromethane to give 1.1 g of off-white solid with mp 122°–124° C.

Calc for: $C_{18}H_{14}Cl_2N_2O$: C, 62.60, H, 4.09, N, 8.12. Found: C, 62.50, H, 4.11, N, 7.90.

Example 15

2-(3,5-dichlorothiobenzoyl)-3,4,4a,5,6,7-hexahydro-2H-benzo[6,7]cyclohepta[1,2c]pyridazine 2-(3,5-dichlorobenzoyl)-3,4,4a,5,6,7-hexahydro-2H-benzo[6,7]cyclohepta[1,2c]pyridazine of Example 7 (1.22 g, 3.27 mmol) and phosphorous pentasulfide (2.14 g, 3.9 mmol) were combined in 200 mL of toluene and heated to 100° C. for 1 h. The mixture was cooled and filtered through a pad of silica gel and washed with dichloromethane. The filtrate was evaporated to dryness and purified by column chromatography eluted with dichloromethane to give 1.2 g of yellow solid which was recrystallized from ether to give the desired compound (1.0 g) with mp 149°–150° C.

Calc for $C_{20}H_{18}Cl_2N_2S$: C, 61.40, H, 4.66, N, 7.19; found C, 61.67, H, 4.65, N, 7.06.

Example 16

2-(3,4-difluorothiobenzoyl)-3,4,4a,5,6,7-hexahydro-2H-benzo[6,7]cyclohepta[1,2c]pyridazine 2-(3,4-difluorothiobenzoyl)-3,4,4a,5,6,7-hexahydro-2H-benzo[6,7]cyclohepta[1,2c]pyridazine of Example 8 (1.5 g, 4.4 mmol) and phosphorous pentasulfide (1.74 g, 5.3 mmol) were combined in 200 mL of toluene and heated to reflux for 1 h. The mixture was cooled and filtered through a pad of silica gel and washed with dichloromethane. The filtrate was evaporated to dryness and purified by column chromatography eluted with dichloromethane to give 1.3 g of yellow solid which was recrystallized from ether to give the desired compound (0.83 g) with mp 134°–136° C.

Calc for $C_{20}H_{18}F_2N_2S$: C, 67.40, H, 5.09, N, 7.86; found C, 67.28, H, 5.03, N, 7.94.

Example 17

2-(3,4-dichlorothiobenzoyl)-3,4,4a,5,6,7-hexahydro-2H-benzo[6,7]cyclohepta[1,2c]pyridazine 2-(3,4-dichlorobenzoyl)-3,4,4a,5,6,7-hexahydro-2H-benzo[6,7] cyclohepta[1,2c]pyridazine of Example 9 (1.5 g, 4.0 mmol) and phosphorous pentasulfide (2.7 g, 6 mmol) were combined in 150 mL of toluene and heated to 100° C. for 30 min. The mixture was cooled and filtered through a pad of silica gel and washed with dichloromethane. The filtrate was evaporated to dryness and purified by column chromatography eluted with dichloromethane to give 1.3 g of yellow solid which was recrystallized from ether to give the desired compound (1.0 g) with mp 140°–141° C.

Calc for $C_{20}H_{18}Cl_2N_2S$: C, 61.40, H, 4.66, N, 7.19; found C, 61.78, H, 4.69, N, 7.09.

Example 18

3-(3,4-difluorothiobenzoyl)-3,4-diazo-1,2,3,9,10,10a-hexahydrophenanthrene 3-(3,4-difluorobenzoyl)-3,4-diazo-1,2,3,9,10,10a-hexahydrophenanthrene of Example 10 (1.0 g, 3.06 mmol) and phosphorous pentasulfide (2.05 g, 4.6 mmol) were combined in 150 mL of toluene and heated to reflux for 1.5 h. The mixture was cooled and filtered through a pad of silica gel and washed with dichloromethane. The filtrate was evaporated to dryness and purified by column chromatography eluted with dichloromethane to give 0.8 g of yellow solid with mp 170°–171° C.

Calc for $C_{19}H_{16}F_2N_2S$: C, 66.65, H, 4.71, N, 8.18; found C, 66.32, H, 4.76, N, 8.19.

Example 19

3-(3,4-dichlorothiobenzoyl)-3,4-diazo-1,2,3,9,10,10a-hexahydrophenanthrene 3-(3,4-dichlorobenzoyl)-3,4-diazo-1,2,3,9,10,10a-hexahydrophenanthrene of Example 10 (1.06 g, 2.95 mmol) and phosphorous pentasulfide (1.17 g 3.83 mmol) were combined in 150 mL of toluene and heated to reflux for 1.5 h. The mixture was cooled and filtered through a pad of silica gel and washed with dichloromethane. The filtrate was evaporated to dryness and purified by column chromatography eluted with dichloromethane to give 0.8 g of yellow solid with mp 110°–111° C.

Calc for $C_{19}H_{16}Cl_2N_2S$: C, 60.80, H, 4.30, N, 7.46; found C, 60.74, H, 4.11, N, 7.47.

Example 20

3-(3,5-dichlorothiobenzoyl)-3,4-diazo-1,2,3,9,10,10a-hexahydrophenanthrene 3-(3,5-dichlorobenzoyl)-3,4-diazo-1,2,3,9,10,10a-hexahydrophenanthrene of Example 11 (1.5 g, 4.2 mmol) and phosphorous pentasulfide (1.69 g, 4.2 mmol) were combined in 150 mL of toluene and heated to 80° C. for 1 h. The mixture was cooled and filtered through a pad of silica gel and washed with dichloromethane. The filtrate was evaporated to dryness and purified by column chromatography eluted with dichloromethane and recrystallized from ether/hexane to give 1.1 g of yellow solid with mp 162°–163° C.

Calc for $C_{19}H_{16}Cl_2N_2S$: C, 60.80, H, 4.30, N, 7.46; found C, 60.78, H, 4.26, N, 7.22.

Example 21

3-(3,4-dichlorothiobenzoyl)-3,4-diazo-9-oxa-1,2,3,9,10,10a-hexahydrophenanthrene 3-(3,4-dichlorobenzoyl)-3,4-diazo-9-oxa-1,2,3,9,10,10a-hexahydrophenanthrene of Example 12 (0.6 g, 1.66 mmol) and phosphorous pentasulfide (0.96 g 2.1 mmol) were combined in 100 mL of toluene and heated to reflux for 1.5 h. The mixture was cooled and filtered through a pad of silica gel and washed with dichloromethane. The filtrate was evaporated to dryness and purified by column chromatography eluted with dichloromethane to give 0.5 g of yellow solid with mp 187°–188° C.

Calc for $C_{18}H_{14}Cl_2N_2OS$: C, 57.30, H, 3.74, N, 7.43; found C, 57.09, H, 3.75, N, 7.29.

Example 22

3-(3,4-dichlorothiobenzoyl)-3,4-diazo-1,2,3,9,9a-tetrahydrofluorene 3-(3,4-dichlorobenzoyl)-3,4-diazo-1,2,3,9,9a-tetrahydrofluorene of Example 14 (0.63 g, 1.8 mmol) and phosphorous pentasulfide (1.05 g 2.3 mmol) were combined in 100 mL of toluene and heated to reflux for 1.5 h. The mixture was cooled and filtered through a pad of silica gel and washed with dichloromethane. The filtrate was evaporated to dryness and purified by column chromatography eluted with dichloromethane to give 0.5 g of yellow solid with mp 138°–140° C.

Calc for $C_{18}H_{14}Cl_2N_2S$: C, 59.84, H, 3.91, N, 7.76; found C, 59.77, H, 3.97, N, 7.76.

What is claimed is:

1. A compound of the formula:

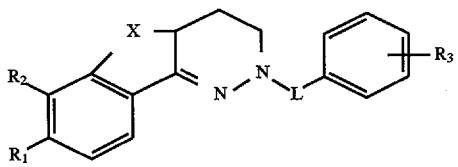

wherein L is selected from the group consisting of CO, CS, and $SO_2$;

wherein $R_1$ and $R_2$ are independently selected from the group consisting of hydrogen, halogen, alkyl ($C_1$–$C_6$), haloalkyl ($C_1$–$C_6$), nitro, cyano, carboxyl and carboalkoxyl ($C_1$–$C_6$); provided that when L is $SO_2R_1$ and $R_2$ are not simultaneously hydrogen;

wherein $R_3$ is independently selected from 1–3 members of the group consisting of hydrogen, halogen, alkyl ($C_1$–$C_6$), haloalkyl ($C_1$–$C_6$), nitro, carboxyl and carboalkoxyl ($C_1$–$C_6$); and wherein X is selected from either $(CH_2)_n$ or $Y(CH_2)_{n-1}$, wherein Y is O or S and n is an integer from 1–3.

2. The compound of claim 1, wherein L is $SO_2$, at least one of $R_1$ and $R_2$ is halogen, $R_3$ is independently selected from any of halogen or $CF_3$ and X is $(CH_2)_n$ wherein n is 1–3.

3. The compound of claim 1, wherein L is CO or CS, $R_1$ and $R_2$ are each hydrogen, $R_3$ is 3,4-dichloro and X is $(CH_2)_n$, wherein n is 1–3.

4. The compound of claim 1, selected form the group consisting of:

8-bromo-3,4,4a,5,6,7-hexahydro-2-(4-iodobenzenesulfonyl)-2H-benzo[6,7]cyclohepta[1,2c]pyridazine; 8-bromo-3,4-diazo-1,2,3,9,10,10a-hexahydro-3-(4-iodobenzenesulfonyl)phenanthrene; 7,8-dibromo-3,4-diazo-1,2,3,10,10a-hexahydro-3-(4-iodobenzene-sulfonyl)phenanthrene; 3-(3,4-dichlorobenzoyl)-3,4-diazo-1,2,3,9,10,10a-hexahydrophenanthrene; and 2-(3,5-dichlorobenzoyl)-3,4,4a,5,6,7-hexahydro-2H-benzo[6,7]cyclohepta[1,2c]pyridazine.

5. A compound of claim 1, selected form the group consisting of:

2-(3,4-difluorothiobenzoyl)-3,4,4a,5,6,7-hexahydro-2H-benzo[6,7]cyclohepta[1,2c]pyridazine; 2-(3,4-dichlorobenzoyl)-3,4,4a,5,6,7-hexahydro-2H-benzo[6,7]cyclohepta[1,2c]pyridazine; 3-(3,4-difluorobenzoyl)-3,4-diazo-1,2,3,9,10,10a-hexahydrophenanthrene; 3-(3,5-dichlorobenzoyl)-3,4-diazo-1,2,3,9,10,10a-hexahydrophenanthrene; and 3-(3,4-dichlorobenzoyl)-3,4-diazo-9-oxa-1,2,3,9,10,10a-hexahydrophenanthrene.

6. The compound of claim 1, selected from the group consisting of:

3-(3,4-dichlorobenzoyl)-3,4-diazo-9-thia-1,2,3,9,10,10a-hexahydrophenanthrene; 3-(3,4-dichlorobenzoyl)-3,4-diazo-1,2,3,9,9a-tetrahydrofluorene; 2-(3,5-dichlorothiobenzoyl)-3,4,4a,5,6,7-hexahydro-2H-benzo[6,7]cyclohepta[1,2c]pyridazine; 2-(3,4-difluorothiobenzoyl)-3,4,4a,5,6,7-hexahydro-2H-benzo[6,7]cyclohepta [1,2c]pyridazine; and 2-(3,4-dichlorothiobenzoyl)-3,4,4a,5,6,7-hexahydro-2H-benzo[6, 7]cyclohepta[1,2c]pyridazine.

7. The compound of claim 1, selected from the group consisting of:

3-(3,4-difluorothiobenzoyl)-3,4-diazo-1,2,3,9,10,10a-hexahydrophenanthrene; 3-(3,4-dichlorothiobenzoyl)-3,4-diazo-1,2,3,9,10,10a-hexahydrophenanthrene; 3-(3,5-dichlorothiobenzoyl)-3,4-diazo-1,2,3,9,10,10a-hexahydrophenanthrene; 3-(3,4-dichlorothiobenzoyl)-3,4-diazo-9-oxa-1,2,3,9,10,10a-hexahydrophenanthrene; 7-chloro-3,4-diazo-1,2,3,9,10,10a-hexahydro-3-(4-iodobenzenesulfonyl)phenanthrene; 7-chloro-3,4-diazo-1,2,3,9,10,10a-hexahydro-3-(2,5-dichlorobenzenesulfonyl)phenanthrene and 3-(3,4-dichlorothiobenzoyl)-3,4-diazo-1,2,3,9,9a-tetrahydrofluorene.

8. The process for preparing a compound of the formula:

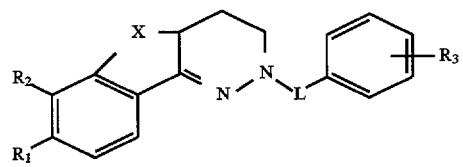

wherein $R_1$, $R_2$, $R_3$, L and X are as defined in claim 1, which comprises: (a) reacting a benzocycloalkanone of the formula:

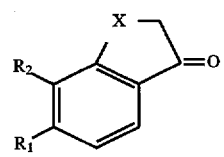

with glyoxylic acid, reducing the product formed with a reducing agent and treating the reduction product formed with hydrazine to form a cyclic acylhydrazone of the formula:

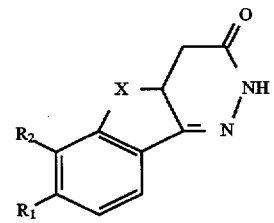

reacting the cyclic acylhydrazone with a second reducing agent to form a cyclic hydrazone of the formula:

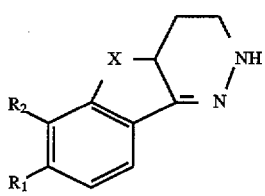

and reacting the cyclic hydrazone with an acylating agent and, where L is CS, (b) reacting the amide formed with a reagent selected from Lawesons Reagent or $P_2S_5$.

9. The process of claim 8, wherein the first reducing agent is zinc in acetic acid.

10. The process of claim 8, wherein the second reducing agent is selected from lithium aluminum hydride and diborane.

11. The process of claim 8, wherein the acylating agent is selected from benzoyl halide and sulfonyl halide.

12. The process of claim 11, wherein the acylating agent is a benzenesulfonyl chloride.

13. The process of claim 11, wherein the acylating agent is a benzoylchloride.

14. A pharmaceutical composition comprising a therapeutically effective amount of the compound of claim 1 in combination with a pharmaceutically acceptable carrier.

15. A method of treating any of contraception, pregnancy termination, labor induction or osteoporosis comprising administering the compound of claim 1 to a patient in a therapeutically effective amount for treating any of contraception, pregnancy termination, labor induction or osteoporosis.

16. The method of claim 15, wherein the amount is 1–500 mg/kg/day.

* * * * *